United States Patent [19]
Bandman et al.

[11] Patent Number: 6,015,788
[45] Date of Patent: Jan. 18, 2000

[54] HUMAN NUCLEIC ACID BINDING PROTEIN

[75] Inventors: Olga Bandman, Mountain View; Janice Au-Young, Berkeley; Phillip R. Hawkins, Mountain View; Jennifer L. Hillman, San Jose, all of Calif.

[73] Assignee: Incyte Pharmaceuticals, Inc., Palo Alto, Calif.

[21] Appl. No.: 09/195,855

[22] Filed: Nov. 19, 1998

Related U.S. Application Data

[62] Division of application No. 08/698,407, Aug. 15, 1996, Pat. No. 5,856,128.

[51] Int. Cl.$^7$ .................................................. A61K 38/00
[52] U.S. Cl. .............................. 514/12; 514/2; 530/350; 530/324; 435/69.1
[58] Field of Search .......................... 514/12, 2; 530/350, 530/324; 435/69.1

[56] References Cited

U.S. PATENT DOCUMENTS 5,856,128   1/1999   Bandman et al. ..................... 435/69.1

OTHER PUBLICATIONS

Stryer, L. (1981) Biochemistry, WH Freeman and Company, New York, San Francisco.
Pang et al. (1993) GenBank Database, Accession No. S33706.
Zamore et al. (1994) GenBank Database, Accession No. S20250.
Fisher, D.E., et al., "Pulse labeling of small nuclear ribonucleoproteins in vivo reveals distinct patterns of antigen recognition by human autoimmune antibodies", *Proc. Natl. Acad. Sci.*, 81:3185–3189 (1984).
Hermann, H., et al., "snRNP Sm proteins share two evolutionarily conserved sequence motifs which are involved in Sm protein–protein interactions", *EMBO J.*, 14:2076–2088 (1995).
Kanaar, R., et al., "The Conserved Pre–mRNA Splicing Factor U2AF from Drosophila: Requirement for Viability", *Science*, 262:569–573 (1993).
Koren, E., "Murine and Human Antibodies to Native DNA That Cross–React with the A and D SnRNP Polypeptides Cause Direct Injury of Cultured Kidney Cells", *J. Immunol.*, 154:4857–4864 (1995).

Lee, C.G., et al., "RNA Annealing Activity Is Intrinsically Associated with U2AF", *J. Biol. Chem.*, 268:13472–13478 (1993).

Pang, Q., et al., "Two cDNAs from the plant *Arabidopsis thaliana* that partially restore recombination proficiency and DNA–damage resistance to *E. coli* mutants lacking recombination–intermediate–resolution activities", *Nuc. Acids Res.*, 21:1647–1653 (1993).

Tsukahara, T., et al., "Regulation of alternative splicing in the amyloid precursor protein (APP) mRNA during neuronal and glial differentiation of P19 embryonal carcinoma cells" *Brain Res.*, 679:178–183 (1995).

Zamore, P.D., et al., "Cloning and domain structure of the mammalian splicing factor U2AF", *Nature*, 355:609–614 (1992).

Hu, Y. et al., (GI 1809248) GenBank Sequence Database (Accession U51586) National Center for Biotechnology Information: National Library of Medicine, Bethesda, Maryland 20894 (Direct Submission) (1996).

*Primary Examiner*—Bradley Sisson
*Assistant Examiner*—Enrique D. Longton
*Attorney, Agent, or Firm*—Susan K. Sather; Incyte Pharmaceuticals, Inc.

[57] ABSTRACT

The present invention provides polynucleotides which identify and encode a novel human nucleic acid binding protein (NABP). The invention provides for genetically engineered expression vectors and host cells comprising the nucleic acid sequences encoding NABP. The invention also provides for the use of substantially purified NABP or its antagonists, in pharmaceutical compositions for the treatment of diseases associated with the expression of NABP. Additionally, the invention provides for the use of antisense molecules to NABP in pharmaceutical compositions for treatment of diseases associated with the expression of NABP. The invention also describes diagnostic assays which utilize diagnostic compositions comprising the polynucleotide, fragments or the complement thereof, which hybridize with the genomic sequence or the transcript of polynucleotides encoding NABP or anti-NABP antibodies which specifically bind to NABP.

2 Claims, 11 Drawing Sheets

```
       11            20            29            38            47            56
5' CAT CAC TTA CCA CTA GTT TTA CAT CGT CGT GAC TGG TGC AAA CCC TAG GCT GTT 65            74            83            92           101           110
ACC CAC ACG TTA AGT CGC CGT TTC AGC ACA TTA GTT GCC GGA GCA GCG GTG CTG 119           128           137           146           155           164
GGT ACC CTG GGC ACA CCT GGA CTG GTG TCC CCA GCA CTG ACC CTG GCC CAG CCC 173           182           191           200           209           218
CTG GGC ACT TTG CCC CAG GCT GTC ATG GCT GCC CAG GCA CCT GGA GTC ATC ACA
                                  M   A   A   Q   A   P   G   V   I   T 227           236           245           254           263           272
GGT GTG ACC CCA GCC CGT CCT CCT ATC CCG GTC ACC ATC CCC TCG GTG GGA GTG
 G   V   T   P   A   R   P   P   I   P   V   T   I   P   S   V   G   V 281           290           299           308           317           326
GTG AAC CCC ATC CTG GCC AGC CCT CCA ACG CTG GGT CTC CTG GAG CCC AAG AAG
 V   N   P   I   L   A   S   P   P   T   L   G   L   L   E   P   K   K
```

FIGURE 1A

```
GAG AAG GAA GAG GAG CTG TTT CCC GAG TCA GAG CGG CCA GAG ATG CTG AGC
 E   K   E   E   E   L   F   P   E   S   E   R   P   E   M   L   S
    335     344     353     362     371     380
GAG CAG GAG CAC ATG AGC ATC TCG GGC AGT AGC GCC CGA CAC ATG GTG CAG
 E   Q   E   H   M   S   I   S   G   S   S   A   R   H   M   V   Q
    389     398     407     416     425     434
AAG CTC CGC AAG CAG GAG TCT ACA GTT CTG CGC AAC ATG GTG GAC
 K   L   R   K   Q   E   S   T   V   L   R   N   M   V   D
    443     452     461     470     479     488
CCC AAG GAC ATC GAT GAT CTG GAA GGG GAG ACA GAG TGT GGC AAG
 P   K   D   I   D   D   L   E   G   E   T   E   C   G   K
    497     506     515     524     533     542
TTC GGG GCC GTG AAC CGC GTC ATC TAC CAA GAG AAA CAA GAG GAG
 F   G   A   V   N   R   V   I   Y   Q   E   K   Q   E   E
    551     560     569     578     587     596
GAT GCA GAA ATC ATT GTC AAG ATC TTT GTG GAG TTT TCC ATA GCC TCT GAG ACT
 D   A   E   I   I   V   K   I   F   V   E   F   S   I   A   S   E   T
    605     614     623     632     641     650
```

FIGURE 1B

```
CAT AAG GCC ATC CAG GCC CTC AAT GGC CGC TGG TTT GCT GGC CGC AAG TGG TGG
 H   K   A   I   Q   A   L   N   G   R   W   F   A   G   R   K   W   W

CTG AAG TGT ACG ACC AGG AGC GTT TTG ATA ACA GTG ACC TCT CTG CGT GAC AGT
 L   K   C   T   T   R   S   V   L   I   T   V   T   S   L   R   D   S

GGT CCC TCT CCC CGG ACT TGC ACT TGT TCC TTG TTT CCT CTG GGT TTT ATA GTG
 G   P   S   P   R   T   C   T   C   S   L   F   P   L   G   F   I   V

ATA CAG TGG TGT CCC CGG GGC CAG TCT GCC CAG CCC AGC CTA CAG TGC
 I   Q   W   C   P   R   G   Q   S   A   R   S   Q   P   S   L   Q   C

GGA TAA AGG TGC GGA TGC TGC TGG CCC TG 3'
 G
```

FIGURE 1C

The Electronic Northern for Clone: 609036
and Stringency >= 50

| Library | Lib Description | Abun | Pct Abun |
|---|---|---|---|
| OVARTUM01 | ovarian tumor, 36 F, NORM, WM | 1 | 0.2695 |
| HIPONOT01 | brain, hippocampus, 72 F | 1 | 0.0535 |
| MYOMNOT01 | uterus, myometrium, 43 F | 1 | 0.0409 |
| CARDNOT01 | heart, 65 M | 1 | 0.0398 |
| PROSTUT03 | prostate tumor, 67 M, match to PROSNOT05 | 1 | 0.0352 |
| PANCNOT04 | pancreas, 5 M | 2 | 0.0338 |
| OVARTUT01 | ovarian tumor, 43 F, match to OVARNOT03 | 1 | 0.0323 |
| FIBRSEM01 | fibroblasts, senescent, NORM, WM | 1 | 0.0312 |
| PROSTUT05 | prostate tumor, 69 M, match to PROSNOT07 | 1 | 0.0303 |
| COLNTUT06 | large intestine, cecal tumor, 45 F | 1 | 0.0293 |
| LUNGNOT09 | lung, fetal M | 1 | 0.0286 |
| LUNGNOT10 | lung, fetal M | 1 | 0.0261 |
| STOMFET01 | stomach, fetal F | 1 | 0.0255 |
| MMLR1DT01 | macrophages (adher PBMNC), M/F, 24-hr MLR | 1 | 0.0236 |
| KERANOT01 | keratinocytes, neonatal M | 1 | 0.0228 |
| COLNNOT01 | colon, 75 M, match to COLNTUT02 | 1 | 0.0213 |
| SCORNOT01 | spinal cord, 71 M | 1 | 0.0201 |
| MMLR2DT01 | macrophages (adher PBMNC), M/F, 48-hr MLR | 1 | 0.0177 |

FIGURE 2A

| | | |
|---|---|---|
| BRAITUT02 | brain tumor, metastasis, 58 M | 1 | 0.0169 |
| PLACNOT02 | placenta, fetal F | 1 | 0.0168 |
| KIDNNOT05 | kidney, neonatal F | 1 | 0.0161 |
| PGANNOT01 | paraganglia, 46 M | 1 | 0.0160 |
| BRSTNOT02 | breast, 55 F, match to BRSTTUT01 | 1 | 0.0158 |
| BRSTNOT05 | breast, 58 F, match to BRSTTUT03 | 1 | 0.0154 |
| BRSTTUT01 | breast tumor, 55 F, match to BRSTNOT02 | 1 | 0.0151 |
| LUNGAST01 | lung, asthma, 17 M | 1 | 0.0150 |
| BRAITUT01 | brain tumor, oligoastrocytoma, 50 F | 1 | 0.0134 |
| LIVSFEM02 | liver/spleen, fetal M, NORM, WM | 3 | 0.0080 |

Electronic Northern Results returned a total of 28 row(s).

```
 1  M - - - - - - - - - - - - - A A Q A P - - - - - - - - - - -   SEQ ID NO-1
 1  M L G G L Y G D L P P T D D E K P S - - - - - - - - - - - -   SEQ ID NO-3
 1  M - - S D F D E F E R Q L N E N K Q E R D K E N R H R K R S    SEQ ID NO-4
 1  M - - G - Y D D - - - - - - - - - - - R E R D R E R R R H -   SEQ ID NO-5

7  - - - - - - - - - - - - - G V I T G V - - - - - - - - - - -   SEQ ID NO-1
20  - - - - - - - - - - - - G N S S V W S R S T K M A P P T L -   SEQ ID NO-3
29  H S R S R S R D R K R R S H R E R S R D R S A S R D R - - -   SEQ ID NO-4
16  R S R S R D R - - - - - - - - - - - R R N R D Q R S - R N S   SEQ ID NO-5

13  - T P A - - - - - - - - - - - - - - - R P P I P V T I P S V   SEQ ID NO-1
38  R K P P A - - - - - - - - - - - - - - F A P P Q T I L R P L   SEQ ID NO-3
59  R R R S K P L T R G A K E E H G G L I R S P R H E K K K V -   SEQ ID NO-4
37  R R K P - - - - - - - - - - - - - - - - - - - - - - - - - -   SEQ ID NO-5

27  - - - - - - G V V N P - - - - - I L A S P - - - - - - P P -   SEQ ID NO-1
54  - - - N K P K P - - - - - - - - I V S A P Y K P - - - - - -   SEQ ID NO-3
89  R K Y W D V P P P G F E H I T P M Q Y K A M Q A A G Q I P A   SEQ ID NO-4
41  S L Y W D V P P P G F E H I T P M Q Y K A M Q A S G Q I P A   SEQ ID NO-5

37  - P T L G L E P - - - - - - - - - - - - - - - - - V T S S V   SEQ ID NO-1
69  N S S Q S V L I P A N E S A P S H Q P A L V G - L - - - - -   SEQ ID NO-3
119 T A L L P T M T P D G L A V T P T P V P V V G S Q M T R Q A   SEQ ID NO-4
71  S - - - - - - - V V P D T - - P Q T A V P V V G S T I T R Q A SEQ ID NO-5
```

```
45  - - - - - - - - - - - - - - - - - - - - - - - - K K - - - -  SEQ ID NO-1
97  I E E Y D P A R P N D Y E E - - - - - - Y K R E K K - - - -  SEQ ID NO-3
149 R R L Y V G N I P F G I T E E A M M D F F N A Q M R L G G L  SEQ ID NO-4
93  R R L Y V G N I P F G V T E E E M M E F F N Q Q M H L V G L  SEQ ID NO-5

47  - E K E E E - - - - - - - - - - - E L - - - - - - - - - - -  SEQ ID NO-1
117 - R K A T E A E M K R E M D K R R Q V - - - - - - - - - - -  SEQ ID NO-3
179 T Q A P G N P V L A V Q I N Q D K N F A F L E F R S V D E T  SEQ ID NO-4
123 A Q A A G S P V L A C Q I N L D K N F A F L E F R S I D E T  SEQ ID NO-5

54  - - - - - F P E S E R P E - - - - - - - - - - - - - - - - -  SEQ ID NO-1
135 - - - - - Y P E R D M R E R E E R E R R E R E I T V I L S V  SEQ ID NO-3
209 T Q A M A F D G I I F Q G Q S L K I R R P H D Y Q P L P G M  SEQ ID NO-4
153 T Q A M A F D G I N L K G Q S L K I R R P H D Y Q P M P G I  SEQ ID NO-5

62  - - - - - - - - - - - - - - - - - - M L S E Q E H M S I S G  SEQ ID NO-1
160 - D I S G E E R G R D P A R V V V E V L G R E D P R L L P G  SEQ ID NO-3
239 S E - - - - N P S V Y V P G V V S T V V P D S A H K L F I G  SEQ ID NO-4
183 T D T P A I K P A V V S S G V I S T V V P D S P H K I F I G  SEQ ID NO-5

74  S - - - - - - - - - - - - - - - - - - - - - - - - - - - - -  SEQ ID NO-1
189 N V D G F - - - - - - - - - - - S I G K S K P S G L G V G A  SEQ ID NO-3
265 G L P N Y L N D D Q V K E L L T S F G P L K A F N L V K D S  SEQ ID NO-4
213 G L P N Y L N D D Q V K E L L L S F G K L R A F N L V K D A  SEQ ID NO-5
```

```
75   ---SAR------HMVMQKLLRKQE----------------  SEQ ID NO-1
208  GGQMTPA----QRMMPKMGWKQGQ----LGKSE         SEQ ID NO-3
295  ATGLSKGYAFCEYVDINVTDQAIAGLNGMQ            SEQ ID NO-4
243  ATGLSKGYAFCEYVDLSITDQSIAGLNGMQ            SEQ ID NO-5

90   ----------------------------------------  SEQ ID NO-1
234  QGIPTPLMAKKT--DRRAGVIVNASENKSS            SEQ ID NO-3
325  LGDKKLLVQRASVGAKNATLVSPPSTINQT            SEQ ID NO-4
273  LGDKKLIVQRASVGAKNA---QNAANTTQ             SEQ ID NO-5

90   -----------------------STVMLRNMV          SEQ ID NO-1
262  SAEKKVV---KSVNINGEPTRVLLLRNMV             SEQ ID NO-3
355  PVTLQVPGLMSSQVQMGGHPTEVLCLMNMV            SEQ ID NO-4
299  SVMLQVPGL--SNVVTSGPPTEVLCLLNMV            SEQ ID NO-5

100  ----------------GEVTEECGKFGAVNR           SEQ ID NO-1
288  DPKDIDDDLE-----DEVGGECAKYGTVTR            SEQ ID NO-3
385  LPEELLDDEEYEEIHVEDVRDECSKYGLVKS           SEQ ID NO-4
327  TPDELRDEEEYEDILEDIKEECTKYGVVRS            SEQ ID NO-5

125  VIIYQEKQGEEEDAEIIVKIFVEFSIASETT           SEQ ID NO-1
313  VLIFEITEPNFPVHEAV-RIFVQFSRPEET            SEQ ID NO-3
415  IEI---PRPVDGVEVPGCGKIFVEFTSVFDC           SEQ ID NO-4
357  VEI---PRPIEGVEVPGCGKVFVEFNSVLDC           SEQ ID NO-5
```

| | | | | | | | | |
|---|---|---|---|---|---|---|---|---|
| 155 | H K A I Q A L N G R W F A G R K W W L K C T T R S V L I T V | SEQ ID NO-1 |
| 342 | T K A L V D L D G R Y F G G R - - - - - - T V R A T F Y D E | SEQ ID NO-3 |
| 443 | Q K A M Q G L T G R K F A N R - - - - - - V V V T K Y C D P | SEQ ID NO-4 |
| 385 | Q K A Q Q A L T G R K F S D R - - - - - - V V V T S Y F D P | SEQ ID NO-5 |
| | | |
| 185 | T S L R D S G P S P R T C T C S L F P L G F I V I Q W C P R | SEQ ID NO-1 |
| 366 | E K F S K N E L A P V - - - - - - - - - - - - - - - W - - | SEQ ID NO-3 |
| 467 | D S Y H R R D - - - - - - - - - - - F - - - - - - - - - - | SEQ ID NO-4 |
| 409 | D K Y H R R E - - - - - - - - - - - F - - - - - - - - - - | SEQ ID NO-5 |
| | | |
| 215 | G Q A R S A Q P S L Q C G | SEQ ID NO-1 |
| 377 | - - - - - - - - - - - - | SEQ ID NO-3 |
| 475 | - - - - - - - P G E I P G | SEQ ID NO-4 |
| 416 | - - - - - - - - - - - - | SEQ ID NO-5 |

FIGURE 3D

HUMAN NUCLEIC ACID BINDING PROTEIN

This application is a divisional application of U.S. application Ser. No. 08/698,407, filed Aug. 15, 1996, now U.S. Pat. No. 5,856,128.

FIELD OF THE INVENTION

The present invention relates to nucleic acid and amino acid sequences of a novel human nucleic acid binding protein and to the use of these sequences in the diagnosis, study, prevention, and treatment of disease.

BACKGROUND OF THE INVENTION

DNA recombination, DNA repair, and RNA splicing are multistep processes that rely on protein complexes (Coleman JE et al (1980) CRC Crit Rev Biochem 7: 247–289). These complexes may bind, unwind, anneal, cleave, and otherwise modify DNA or RNA. Typically, several protein subunits contribute to these complexes.

In a search for molecules that enable plants to resist the DNA damaging effects of ultraviolet radiation, researchers discovered the *Arabidoesis thaliana* Drt111 protein (Pang Q et al (1993) Nuc Acids Res 21: 1647–1653). Drt111 partially restores recombination proficiency and DNA-damage resistance to *E. coli* ruvC mutants, cleaving single-stranded DNA in homologous recombination intermediates (Holliday junctions).

Nucleic acid binding and modifying proteins are also required for splicing pre-mRNA in the cell nucleus. One such protein is the U2 snRNP auxiliary factor (U2AF) which has been shown to bind pre-mRNA (Zamore P et al (1992) Nature 355: 609–614). U2AF belongs to a family of splicing factor genes that possess multiple repeats of the RS dipeptide at either their N or C terminus. The RS domain has been shown to be essential for annealing complementary RNA or DNA sequences and for binding RNA (Lee CG et al (1993) J Biol Chem 268: 13472–13478).

Nucleic Acid Binding Proteins and Disease

One of the hallmarks of Alzheimer's disease is the deposition of a processed form of amyloid precursor protein (APP) outside of brain cells (Soto C et al (1994) J Neurochem 63: 1191–1198). As P19 EC cells differentiate into glial cells, expression of U2AF is reduced and APP is alternatively spliced. Transfection with U2AF restores the original APP splice variant, thus U2AF is believed to play a critical role in glial-specific splicing of APP (Tsukahara T et al (1995) Brain Res 679: 178–183).

Auto-antibodies against snRNPs were found to be common in systemic lupus erythematosus (SLE) and related autoimmune disorders (Fisher DE et al (1984) Proc Natl Acad Sci 81: 3185–3189). Later, auto-antibodies to U2 snRNP and the other snRNPs were found to be diagnostic for SLE (Hermann H et al EMBO J 14: 2076–2088). In cell culture experiments, Koren et al (1995, J Immunol 154: 4857–4864) found that antibodies derived from a murine model for SLE were pathogenic only when they had reactivity with snRNP components. Thus, an autoimmune response to snRNP components appears to be important in SLE pathology.

More than a million Americans suffer from dementia, a permanent and often progressive decline in intellectual function that substantially interferes with a person's social and economic activity. Alzheimer's disease is a major cause of dementia and its prevalence is growing. Currently, there are no known treaments that stop or reverse the relentless progression in the impairment in mental abilities of Alzheimer's disease patients. Similarly, there are no known treatments that permanently end SLE. Current treatments for SLE control the inflammatory responses that are a consequence of SLE, but do not mask the antigen that promotes the production of self-reactive immune cells. Thus, a new nucleic acid binding protein would satisfy this need in the art by providing new agents for the diagnosis and treatment of Alzheimer's disease and various autoimmune disorders such as SLE.

SUMMARY

The present invention discloses a novel human nucleic acid binding protein (hereinafter referred to as NABP), characterized as having homology to *Arabidopsis thaliana* Drt111 (GI 166694) and human and Drosophila U2 snRNP auxiliary factor large subunits (GI 267188 and GI 627165, respectively). Accordingly, the invention features a substantially purified nucleic acid binding protein, as shown in amino acid sequence of SEQ ID NO:1, and having characteristics of nucleic acid binding proteins.

One aspect of the invention features isolated and substantially purified polynucleotides which encode NABP. In a particular aspect, the polynucleotide is the nucleotide sequence of SEQ ID NO:2. In addition, the invention features polynucleotide sequences that hybridize under stringent conditions to SEQ ID NO:2.

The invention further relates to nucleic acid sequences encoding NABP, oligonucleotides, peptide nucleic acids (PNA), fragments, portions or antisense molecules thereof, and expression vectors and host cells comprising polynucleotides which encode NABP. The present invention also relates to antibodies which bind specifically to NABP, pharmaceutical compositions comprising substantially purified NABP, fragments thereof, or antagonists of NABP, in conjunction with a suitable pharmaceutical carrier, and methods for producing NABP, fragments thereof, or antagonists of NABP.

BRIEF DESCRIPTION OF THE FIGURES

FIGS. 1A, 1B, and 1C show the amino acid sequence (SEQ ID NO:1) and nucleic acid sequence (SEQ ID NO:2) of the novel nucleic acid binding protein, NABP. The alignment was produced using MACDNASIS software (Hitachi Software Engineering Co Ltd, San Bruno, Calif.).

FIGS. 2A and 2B shows the northern analysis for Incyte Clone 609036. The northern analysis was produced electronically using LIFESEQ database (Incyte Pharmaceuticals, Palo Alto Calif.).

FIGS. 3A, 3B, 3C, and 3D show the amino acid sequence alignments among NABP (SEQ ID NO:1), *A. thaliana* Drt111 (GI 166694; SEQ ID NO:3), human U2 snRNP auxiliary factor large subunit (GI 267188; SEQ ID NO:4), and Drosophila snRNP auxiliary factor large subunit (GI 627165; SEQ ID NO:5) produced using the multisequence alignment program of DNASTAR software (DNAStar Inc. Madison Wis.).

DETAILED DESCRIPTION OF THE INVENTION

Definitions

Figure 4:
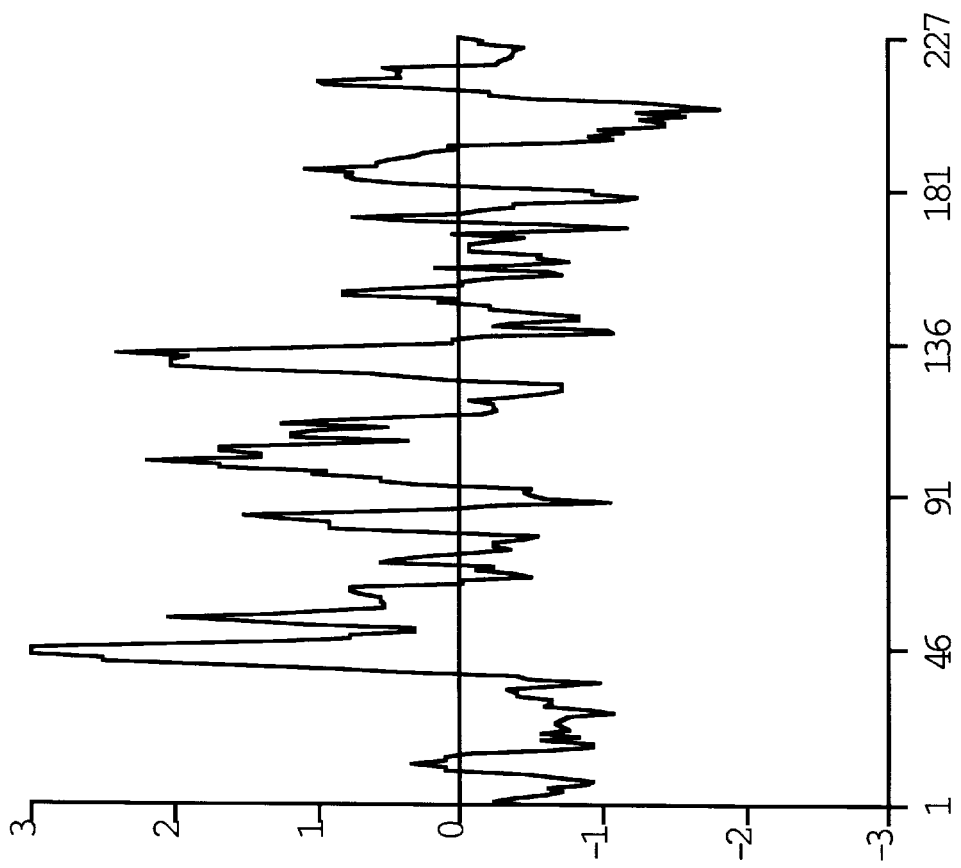
FIG. 4 shows the hydrophobicity plot (generated using MACDNASIS software) for NABP, SEQ ID NO:1. The X axis reflects amino acid position, and the negative Y axis reflects hydrophobicity (same in FIG. 5).

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to peptide or protein sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen PE et al (1993) Anticancer Drug Des 8: 53–63).

As used herein, NABP refers to the amino acid sequences of substantially purified NABP obtained from any species, particularly mammalian, including bovine, ovine, porcine, murine, equine, and preferably human, from any source whether natural, synthetic, semi-synthetic or recombinant.

A "variant" of NABP is defined as an amino acid sequence that is altered by one or more amino acids. The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

A "deletion" is defined as a change in either amino acid or nucleotide sequence in which one or more amino acid or nucleotide residues, respectively, are absent.

An "insertion" or "addition" is that change in an amino acid or nucleotide sequence which has resulted in the addition of one or more amino acid or nucleotide residues, respectively, as compared to the naturally occurring NABP.

A "substitution" results from the replacement of one or more amino acids or nucleotides by different amino acids or nucleotides, respectively.

The term "biologically active" refers to an NABP having structural, regulatory or biochemical functions of a naturally occurring NABP. Likewise, "immunologically active" defines the capability of the natural, recombinant or synthetic NAHP, or any oligopeptide thereof, to induce a specific immune response in appropriate animals or cells and to bind with specific antibodies.

The term "derivative" as used herein refers to the chemical modification of a nucleic acid encoding NABP or the encoded NABP. Illustrative of such modifications would be replacement of hydrogen by an alkyl, acyl, or amino group. A nucleic acid derivative would encode a polypeptide which retains essential biological characteristics of natural NABP.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

"Stringency" typically occurs in a range from about Tm-5° C. (5° C. below the Tm of the probe)to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs J (1994) *Dictionary of Biotechnology*, Stockton Press, New York N.Y.). Amplification as carried out in the polymerase chain reaction technologies is described in Dieffenbach CW and GS Dveksler (1995, *PCR Primer, a Laboratory Manual*, Cold Spring Harbor Press, Plainview N.Y.).

Preferred Embodiments

The present invention relates to a novel human nucleic acid binding protein and to the use of the nucleic acid and amino acid sequences in the study, diagnosis, prevention and treatment of disease. cDNAs encoding a portion of NABP were found in cDNA libraries from a variety of tissues including many types of tumors (FIGS. 2A and 2B).

The present invention also encompasses NABP variants. A preferred NABP variant is one having at least 80% amino acid sequence similarity to the NABP amino acid sequence (SEQ ID NO:1), a more preferred NABP variant is one having at least 90% amino acid sequence similarity to SEQ ID NO:1 and a most preferred NABP variant is one having at least 95% amino acid sequence similarity to SEQ ID NO:1.

Nucleic acids encoding the human nucleic acid binding protein of the present invention were first identified in cDNA, Incyte Clones 609036 (SEQ ID NO:2) from the colon tissue library, COLNNOT01, through a computer-generated search for amino acid sequence alignments. The following Incyte clones (and cDNA libraries from which they were derived) were extended and assembled to create the consensus sequence (SEQ ID NO:2): 60936 (COLNNOT01); 242897 (HIPONOT01); 284323 (CARDNOT01); 454485 (KERANOT01); 518848 (MMLR1DT01); 523888 (MMLR2DT01); 554053 (SCORNOT01); 603191 (BRSTN2T1); 618337 (PGANNOT01); 758021 (BRAITUT02); 779444 (MYOMNOT01); 789689 (PROSTUT3); 817073 (OVARTUT01); 841557 (PROSTUT05); 868692 (LUNGAST01); 958268 (KIDNNOT05); 969065 (BRSTN5T3); 978194 (BRSTN2T1); 1355140 (LUNGNOT09); 1375382 (LUNGNOT10); 1231587 (BRAITUT01); and 1303488 (PLACNOT02). The nucleic acid sequence of SEQ ID NO:2 encodes the NABP amino acid sequence, SEQ ID NO:1.

Figure 5:
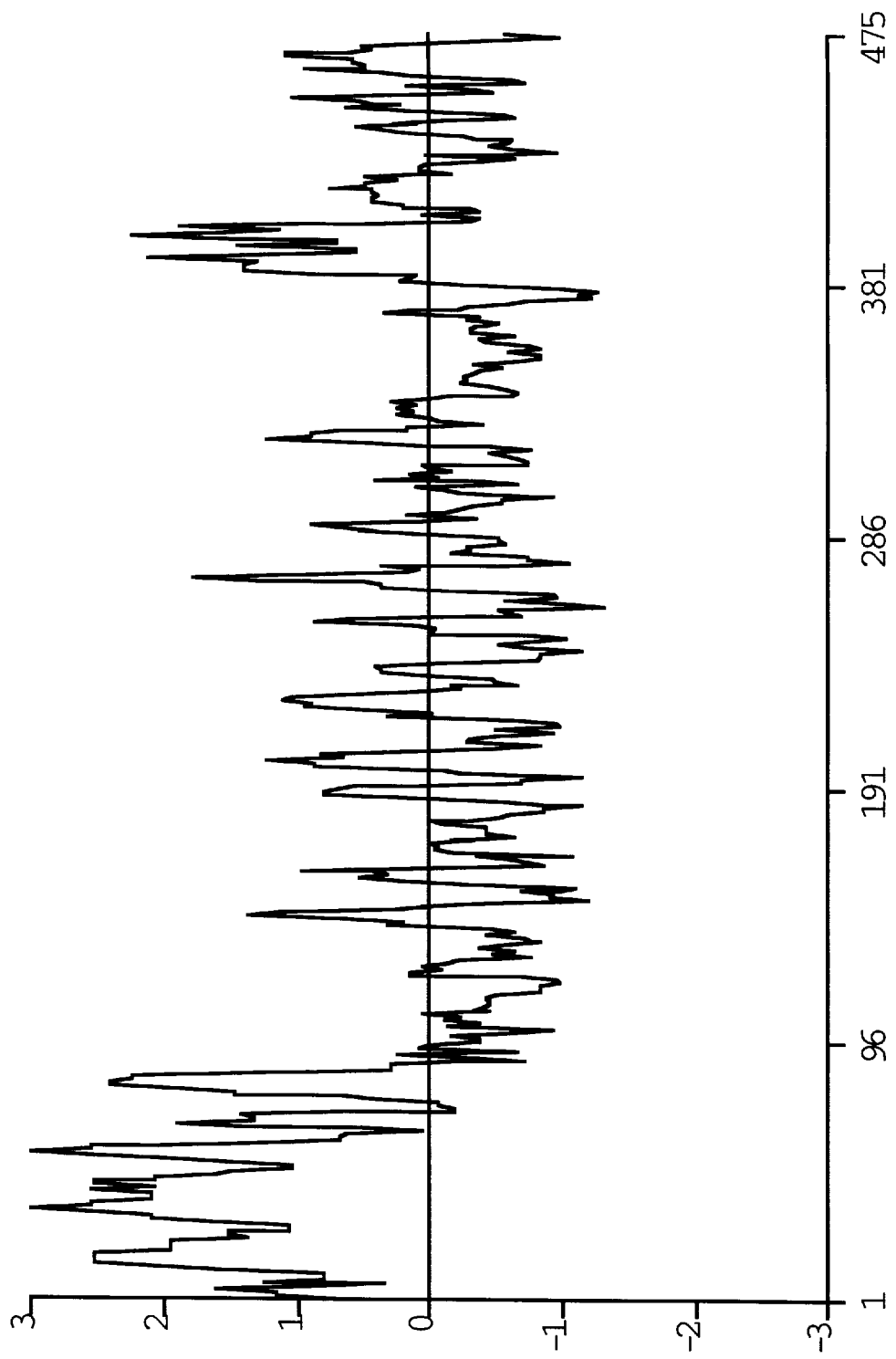
FIG. 5 shows the hydrophobicity plot for human U2 snRNP auxiliary factor large subunit, SEQ ID NO:4.

The present invention is based, in part, on the chemical and structural homology among NABP, *A. thaliana* Drt111 (GI 166694; Pang et al, supra), the human U2 snRNP auxiliary factor large subunit (GI 267188; Zamore et al, supra), and the Drosophila U2 snRNP auxiliary factor large subunit (GI 627165; Kanaar R et al (1993) Science 262: 569–573; FIGS. 3A, 3B, 3C and 3D). The novel NABP is 227 amino acids long and shares 29% identity with Drt111, and 21% identity, with human U2 snRNP auxiliary factor large subunit. NABP has 2 RS amino acid repeats near its C terminus (FIGS. 1A, 1B, and 1C). As illustrated by FIGS. 4 and 5, NABP and the carboxy-terminal region of the human U2 snRNP auxiliary factor large subunit have similar hydrophobicity plots suggesting similar structure.

The NABP Coding Sequences

The nucleic acid and deduced amino acid sequences of NABP are shown in FIGS. 1A, 1B and 1C. In accordance with the invention, any nucleic acid sequence which encodes the amino acid sequence of NABP can be used to generate recombinant molecules which express NABP. In a specific embodiment described herein, a nucleotide sequence encoding a portion of NABP was first isolated as Incyte Clone 609036 from a colon tissue cDNA library (COLNNOT01).

It will be appreciated by those skilled in the art that as a result of the degeneracy of the genetic code, a multitude of NABP-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence of naturally occurring NABP, and all such variations are to be considered as being specifically disclosed.

Although nucleotide sequences which encode NABP and its variants are preferably capable of hybridizing to the nucleotide sequence of the naturally occurring NABP under appropriately selected conditions of stringency, it may be advantageous to produce nucleotide sequences encoding NABP or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding NABP and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding an NABP and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a sequence encoding NABP or any portion thereof.

Also included within the scope of the present invention are polynucleotide sequences that are capable of hybridizing to the nucleotide sequences of FIGS. 1A, 1B and 1C under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymoloay*, Vol 152, Academic Press, San Diego, Calif. incorporated herein by reference, and confer may be used at a defined stringency.

Altered nucleic acid sequences encoding NABP which may be used in accordance with the invention include deletions, insertions or substitutions of different nucleotides resulting in a polynucleotide that encodes the same or a functionally equivalent NABP. The protein may also show deletions, insertions or substitutions of amino acid residues which produce a silent change and result in a functionally equivalent NABP. Deliberate amino acid substitutions may be made on the basis of similarity in polarity, charge, solubility, hydrophobicity, hydrophilicity, and/or the amphipathic nature of the residues as long as the biological activity of NABP is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of NABP. As used herein, an "allele" or "allelic sequence" is an alternative form of NABP. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, SEQUENASE (US Biochemical Corp, Cleveland Ohio)), Taq polymerase (Perkin Elmer, Norwalk Conn.), thermostable T7 polymerase (Amersham, Chicago Ill.), or combinations of recombinant polymerases and proofreading exonucleases such as the ELONGASE amplification system marketed by Gibco BRL (Gaithersburg Md.). Preferably, the process is automated with machines such as the Hamilton MICROLAB 2200 (Hamilton, Reno Nev.), Peltier thermal cycler (PTC200; MJ Research, Watertown Me.) and the ABI 377 DNA sequencers (Perkin Elmer).

Extending the Polynuclootide Sequnce

The polynucleotide sequence encoding NABP may be extended utilizing partial nucleotide sequence and various methods known in the art to detect upstream sequences such as promoters and regulatory elements. Gobinda et al (1993; PCR Methods Applic 2: 318—22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16: 8186). The primers may be designed using OLIGO® 4.06 primer analysis Software (1992; National Biosciences Inc, Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1: 111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequences is that of Parker JD et al (1991; Nucleic Acids Res 19: 3055–60). Additionally, one can use PCR, nested primers and PromoterFinder libraries to walk in genomic DNA (PROMOTOR FINDER™ Clontech (Palo Alto Calif.). This process avoids the need to screen libraries and is useful in finding intron/exon junctions.

Preferred libraries for screening for full length cDNAs are ones that have been size-selected to include larger cDNAs.

Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze the size or confirm the nucleotide sequence of sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. GENOTYPER and SEQUENCE NAVIGATOR from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez MC et al (1993) Anal Chem 65: 2851–2858).

Expression of the Nucleotide Sequence

In accordance with the present invention, polynucleotide sequences which encode NABP, fragments of the polypeptide, fusion proteins or functional equivalents thereof may be used in recombinant DNA molecules that direct the expression of NABP in appropriate host cells. Due to the inherent degeneracy of the genetic code, other DNA sequences which encode substantially the same or a functionally equivalent amino acid sequence, may be used to clone and express NABP. As will be understood by those of skill in the art, it may be advantageous to produce NABP-encoding nucleotide sequences possessing non-naturally occurring codons. Codons preferred by a particular prokaryotic or eukaryotic host (Murray E et al (1989) Nuc Acids Res 17: 477–508) can be selected, for example, to increase the rate of NABP expression or to produce recombinant RNA transcripts having desirable properties, such as a longer half-life, than transcripts produced from naturally occurring sequence.

The nucleotide sequences of the present invention can be engineered in order to alter an NABP coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant polynucleotides encoding NABP may be ligated to a heterologous sequence to encode a fusion protein. For example, for screening of peptide libraries for inhibitors of NABP activity, it may be useful to encode a chimeric NABP protein that is recognized by a commercially available antibody. A fusion protein may also be engineered to contain a cleavage site located between an NABP sequence and the heterologous protein sequence, so that the NABP may be cleaved and purified away from the heterologous moiety.

In an alternate embodiment of the invention, the coding sequence of NABP may be synthesized, whole or in part, using chemical methods well known in the art (see Caruthers M H et al (1980) Nuc Acids Res Symp Ser 215–23, Horn T et al(1980) Nuc Acids Res Symp Ser 225–32, etc). Alternatively, the protein itself could be produced using chemical methods to synthesize an NABP amino acid sequence, whole or in part. For example, peptide synthesis can be performed using various solid-phase techniques (Roberge JY et al (1995) Science 269: 202–204) and automated synthesis may be achieved, for example, using the ABI 431A peptide synthesizer (Perkin Elmer) in accordance with the instructions provided by the manufacturer.

The newly synthesized peptide can be substantially by preparative high performance liquid chromatography (eg, Creighton (1983) *Proteins, Structures add Molecular Principles*, WH Freeman and Co, New York N.Y.). The composition of the synthetic peptides may be confirmed by amino acid analysis or sequencing (eg, the Edman degradation procedure; Creighton, supra). Additionally the amino acid sequence of NABP, or any part thereof, may be altered during direct synthesis and/or combined using chemical methods with sequences from other proteins, or any part thereof, to produce a variant polypeptide.

Expression System

In order to express a biologically active NABP, the nucleotide sequence encoding NABP or its functional equivalent, is inserted into an appropriate expression vector, ie, a vector which contains the necessary elements for the transcription and translation of the inserted coding sequence.

Methods which are well known to those skilled in the art can be used to construct expression vectors containing an NABP coding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual*, Cold Spring Harbor Press, Plainview N.Y. and Ausubel F M et al (1989) *Current Protocols in Molecular Biology*, John Wiley & Sons, New York N.Y.

A variety of expression vector/host systems may be utilized to contain and express an NABP coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the BLUE-SCRIPT phagemid (Stratagene, LaJolla Calif.) or PSPORT1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of NABP, vectors based on SV40 or EBV may be used with an appropriate selectable marker.

In bacterial systems, a number of expression vectors may be selected depending upon the use intended for NABP. For example, when large quantities of NABP are needed for the induction of antibodies, vectors which direct high level expression of fusion proteins that are readily purified may be desirable. Such vectors include, but are not limited to, the multifunctional *E. coli* cloning and expression vectors such as BLUESCRIPT (Stratagene), in which the NABP coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264: 5503–5509); and the like. PGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153: 516–544.

In cases where plant expression vectors are used, the expression of a 5 sequence encoding NABP may be driven by any of a number of promoters. For example, viral promoters such as the 35S and 19S promoters of CaMV (Brisson et al (1984) Nature 310: 511-514) may be used alone or in combination with the omega leader sequence from TMV (Takamatsu et al (1987) EMBO J 6: 307–311). Alternatively, plant promoters such as the small subunit of RUBISCO (Coruzzi et al (1984) EMBO J 3: 1671–1680; Broglie et al (1984) Science 224: 838–843); or heat shock promoters (Winter J and Sinibaldi R M (1991) Results Probl Cell Differ 17: 85–105) may be used. These constructs can be introduced into plant cells by direct DNA transformation or pathogen-mediated transfection. For reviews of such techniques, see Hobbs S or Murry L E in McGraw Hill *Yearbook of Science and Technology* (1992) McGraw Hill New York N.Y., pp 191–196 or Weissbach and Weissbach (1988) *Methods for Plant Molecular Biology*, Academic Press, New York N.Y., pp 421–463.

An alternative expression system which could be used to express NABP is an insect system. In one such system, *Autographa californica* nuclear polyhedrosis virus (acNPV) is used as a vector to express foreign genes in *Spodoptera frugiperda* cells or in Trichoplusia larvae. The NABP coding sequence may be cloned into a nonessential region of the virus, such as the polyhedrin gene, and placed under control of the polyhedrin promoter. Successful insertion of NABP will render the polyhedrin gene inactive and produce recombinant virus lacking coat protein coat. The recombinant viruses are then used to infect *S. frugiperda* cells or Trichoplusia larvae in which NABP is expressed (Smith et al (1983) J Virol 46: 584; Engelhard E K et al (1994) Proc Nat Acad Sci 91: 3224–7).

In mammalian host cells, a number of viral-based expression systems may be utilized. In cases where an adenovirus is used as an expression vector, an NABP coding sequence may be ligated into an adenovirus transcription/translation complex consisting of the late promoter and tripartite leader sequence. Insertion in a nonessential E1 or E3 region of the viral genome will result in a viable virus capable of expressing NABP in infected host cells (Logan and Shenk (1984) Proc Natl Acad Sci 81: 3655–59). In addition, transcription enhancers, such as the rous sarcoma virus (RSV) enhancer, may be used to increase expression in mammalian host cells.

Specific initiation signals may also be required for efficient translation of an NABP sequence. These signals include the ATG initiation codon and adjacent sequences. In cases where NABP, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20: 125–62; Bittner et al (1987) Methods in Enzymol 153: 516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express NABP may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11: 223–32) and adenine phosphoribosyltransferase (Lowy I et al (1980) Cell 22: 817–23) genes which can be employed in tk- or aprt- cells, respectively. Also, antimetabolite, antibiotic, or herbicide resistance can be used as the basis for selection; for example, dhfr, which confers resistance to methotrexate (Wigler M et al (1980) Proc Natl Acad Sci 77: 3567–70); npt, which confers resistance to the aminoglycosides neomycin and G-418 (Colbere-Garapin F et al (1981) J Mol Biol 150: 1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci 85: 8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C A et al (1995) Methods Mol Biol 55: 121–131).

Identification of Transformants Containing the Polynucleotide Sequence

Although the presence/absence of marker gene expression suggests that the gene of interest is also present, its presence and expression should be confirmed. For example, if the NABP is inserted within a marker gene sequence, recombinant cells containing NABP can be identified by the absence of marker gene function. Alternatively, a marker gene can be placed in tandem with an NABP sequence under the control of a single promoter. Expression of the marker gene in response to induction or selection usually indicates expression of the tandem NABP as well.

Alternatively, host cells which contain the coding sequence for NABP and express NABP may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding NABP can be detected by DNA-DNA or DNA-RNA hybridization or amplification using probes, portions or fragments of polynucleotides encoding NABP. Nucleic acid amplification based assays involve the use of oligonucleotides or oligomers based on the NABP-encoding sequence to detect transformants containing DNA or RNA encoding NABP. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of NABP, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on NABP is preferred, but a competitive binding assay may be employed. These and other assays are described, among other places, in Hampton R et al (1990, *Serological Methods, a Laboratory Manual*, APS Press, St Paul Minn.) and Maddox D E et al (1983, J Exp Med 158: 1211).

A wide variety of labels and conjugation techniques are known by those skilled in the art and can be used in various nucleic acid and amino acid assays. Means for producing labeled hybridization or PCR probes for detecting sequences related to polynucleotides encoding NABP include oligolabeling, nick translation, end-labeling or PCR amplification using a labeled nucleotide. Alternatively, the NABP sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and U.S. Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277, 437; 4,275,149 and 4,366,241. Also, recombinant immunoglobulins may be produced as shown in U.S. Pat. No. 4,816,567 incorporated herein by reference.

Purification of NABP

Host cells transformed with a nucleotide sequence encoding NABP may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing polynucleotides encoding NABP can be designed with signal sequences which direct secretion of NABP through a prokaryotic or eukaryotic cell membrane. Other recombinant constructions may join NABP to nucleotide sequence encoding a polypeptide domain which will facilitate purification of soluble proteins (Kroll D J et al (1993) DNA Cell Biol 12: 441–53; cf discussion of vectors infra containing fusion proteins).

NABP may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and NABP is useful to facilitate purification. One such expression vector provides for expression of a fusion protein compromising an NABP and contains nucleic acid encoding 6 histidine residues followed by thioredoxin and an enterokinase cleavage site. The histidine residues facilitate purification on IMIAC (immobilized metal ion affinity chromatography as described in Porath et al (1992) Protein Expression and Purification 3: 263–281) while the enterokinase cleavage site provides a means for purifying NABP from the fusion protein.

In addition to recombinant production, fragments of NABP may be produced by direct peptide synthesis using solid-phase techniques (cf Stewart et al (1969) *Solid-Phase Pegtide Synthesis*, WH Freeman-Co, San Francisco; Merrifield J (1963) J Am Chem Soc 85: 2149–2154). In vitro protein synthesis may be performed using manual techniques or by automation. Automated synthesis may be achieved, for example, using Applied Biosystems 431A peptide synthesizer (Perkin Elmer, Foster City Calif.) in accordance with the instructions provided by the manufacturer. Various fragments of NABP may be chemically synthesized separately and combined using chemical methods to produce the full length molecule.

Uses of NABP

The rationale for use of the nucleotide and polypeptide sequences disclosed herein is based in part on the chemical and structural homology among the novel NABP disclosed herein, *A. thaliana* Drt111 (GI 166694; Pang et al, supra), human U2 snRNP auxilliary factor large subunit (GI 267188; Zamore et al, supra), and Drosophila U2 snRNP auxilliary factor large subunit (GI 627165; Kanaar et al, supra).

Accordingly, NABP or an NABP derivative may be used to treat Alzheimer's disease and autoimmune disorders, such as SLE. In those conditions where NABP activity is not desirable, cells could be transfected with antisense sequences of NABP-encoding polynucleotides or provided with antagonists of NABP.

NABP Antibodies

NABP-specific antibodies are useful for the diagnosis of conditions and diseases associated with expression of NABP. Such antibodies may include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

NABP for antibody induction does not require biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of NABP amino acids may be fused with those of another protein such as keyhole limpet hemocyanin and antibody produced against the chimeric molecule. Procedures well known in the art can be used for the production of antibodies to NABP.

For the production of antibodies, various hosts including goats, rabbits, rats, mice, etc may be immunized by injection with NABP or any portion, fragment or oligopeptide which retains immunogenic properties. Depending on the host species, various adjuvants may be used to increase immunological response. Such adjuvants include but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium paryum* are potentially useful human adjuvants.

Monoclonal antibodies to NABP may be prepared using any technique which provides for the production of antibody molecules by continuous cell lines in culture. These include but are not limited to the hybridoma technique originally described by Koehler and Milstein (1975 Nature 256: 495–497), the human B-cell hybridoma technique (Kosbor et al (1983) Immunol Today 4:72; Cote et al (1983) Proc Natl Acad Sci 80: 2026–2030) and the EBV-hybridoma technique (Cole et al (1985) *Monoclonal Antibodies and Cancer Therapy*, Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81: 6851–6855; Neuberger et al (1984) Nature 312: 604–608; Takeda et al (1985) Nature 314: 452–454). Alternatively, techniques described for the production of single chain antibodies (U.S. Pat. No. 4,946,778) can be adapted to produce NABP-specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349: 293–299).

Antibody fragments which contain specific binding sites for NABP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W D et al (1989) Science 256: 1275–1281).

A variety of protocols for competitive binding or immunoradiometric assays using either polyclonal or monoclonal antibodies with established specificities are well known in the art. Such immunoassays typically involve the formation of complexes between NABP and its specific antibody and the measurement of complex formation. A two-site, monoclonal-based immunoassay utilizing monoclonal antibodies reactive to two noninterfering epitopes on a specific NABP protein is preferred, but a competitive binding assay may also be employed. These assays are described in Maddox DE et al (1983, J Exp Med 158: 1211).

Diagnostic Assays Using NABP Specific Antibodies

Particular NABP antibodies are useful for the diagnosis of conditions or diseases characterized by expression of NABP or in assays to monitor patients being treated with NABP, agonists or inhibitors. Diagnostic assays for NABP include methods utilizing the antibody and a label to detect NABP in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring NABP, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on NABP is preferred, but a competitive binding assay may be employed. These assays are described, among other places, in Maddox, D E et al (1983, J Exp Med 158: 1211).

In order to provide a basis for diagnosis, normal or standard values for NABP expression must be established. This is accomplished by combining body fluids or cell extracts taken from normal subjects, either animal or human, with antibody to NABP under conditions suitable for complex formation which are well known in the art. The amount of standard complex formation may be quantified by comparing various artificial membranes containing known quantities of NABP with both control and disease samples from biopsied tissues. Then, standard values obtained from normal samples may be compared with values obtained from samples from subjects potentially affected by disease. Deviation between standard and subject values establishes the presence of disease state.

Drug Screening

NABP, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between NABP and the agent being tested, may be measured.

Another technique for drug screening which may be used provides for high throughput screening of compounds having suitable binding affinity to the NABP is described in detail in "Determination of Amino Acid Sequence Antigenicity" by Geysen H N, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of NABP and washed. Bound NABP is then detected by methods well known in the art. Purified NABP can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding NABP specifically compete with a test compound for binding NABP. In this manner, the antibodies can be used to detect the presence of any peptide which shares one or more antigenic determinants with NABP.

Uses of the Polynucleotide Encoding NABP

A polynucleotide encoding NABP, or any part thereof, may be used for diagnostic and/or therapeutic purposes. For diagnostic purposes, polynucleotides encoding NABP of this invention may be used to detect and quantitate gene expression in biopsied tissues in which expression of NABP may be implicated. The diagnostic assay is useful to distinguish between absence, presence, and excess expression of NABP and to monitor regulation of NABP levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding NABP or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring sequences encoding NABP, alleles or related sequences.

Probes may also be used for the detection of related sequences and should preferably contain at least 50% of the nucleotides from any of these NABP encoding sequences. The hybridization probes of the subject invention may be derived from the nucleotide sequence of SEQ ID NO:2 or from genomic sequence including promoter, enhancer elements and introns of the naturally occurring NABP. Hybridization probes may be labeled by a variety of reporter groups, including radionuclides such as 32P or 35S, or enzymatic labels such as alkaline phosphatase coupled to the probe via avidin/biotin coupling systems, and the like.

Other means for producing specific hybridization probes for DNAs encoding NABP include the cloning of nucleic acid sequences encoding NABP or NABP derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Polynucleotide sequences encoding NABP may be used for the diagnosis of conditions or diseases with which the expression of NABP is associated. For example, polynucleotide sequences encoding NABP may be used in hybridization or PCR assays of fluids or tissues from biopsies to detect NABP expression. The form of such qualitative or quantitative methods may include Southern or northern analysis, dot blot or other membrane-based technologies; PCR technologies; dip stick, pIN, chip and ELISA technologies. All of these techniques are well known in the art and are the basis of many commercially available diagnostic kits.

The nucleotide sequences encoding NABP disclosed herein provide the basis for assays that detect activation or induction associated with Alzheimer's disease and autoimmune disorders, such as SLE. The nucleotide sequence encoding NABP may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of nucleotide sequences encoding NABP in the sample indicates the presence of the associated disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for NABP expression must be established. This is accomplished by combining body fluids or cell extracts taken from normal subjects, either animal or human, with NABP, or a portion thereof, under conditions suitable for hybridization or amplification. Standard hybridization may be quantified by comparing the values obtained for normal subjects with a dilution series of NABP run in the same experiment where a known amount of a substantially purified NABP is used. Standard values obtained from normal samples may be compared with values obtained from samples from patients afflicted with NABP-associated diseases. Deviation between standard and subject values is used to establish the presence of disease.

Once disease is established, a therapeutic agent is administered and a treatment profile is generated. Such assays may be repeated on a regular basis,to evaluate whether the values in the profile progress toward or return to the normal or standard pattern. Successive treatment profiles may be used to show the efficacy of treatment over a period of several days or several months.

PCR, as described in U.S. Pat. Nos. 4,683,195 and 4,965,188, provides additional uses for oligonucleotides based upon the NABP sequence. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby PC et al 1993 J Immunol Methods 159: 235–44) or biotinylating (Duplaa C et al 1993 Anal Biochem 212: 229–236) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. For example, the presence of a relatively high amount of NABP in extracts of biopsied tissues may indicate the onset of SLE. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

Based upon its homology to genes encoding Drt111 and U2AP, and its expression profile, polynucleotide sequences encoding NABP disclosed herein may be useful in the treatment of conditions such as Alzheimer's disease and autoimmune disorders, such as SLE.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense polynucleotides of the gene encoding NABP. See, for example, the techniques described in Sambrook et al (supra) and Ausubel et al (supra).

The polynucleotides comprising full length cDNA sequence and/or its regulatory elements enable researchers to use sequences encoding NABP as an investigative tool in sense (Youssoufian H and HF Lodish 1993 Mol Cell Biol 13: 98–104) or antisense (Eguchi et al (1991) Annu Rev Biochem 60: 631–652) regulation of gene function. Such technology is now well known in the art, and sense or antisense oligomers, or larger fragments, can be designed from various locations along the coding or control regions.

Genes encoding NABP can be turned off by transfecting a cell or tissue with expression vectors which express high levels of a desired NABP-encoding fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of gene encoding NABP, ie, the promoters, enhancers, and introns. Oligonucleotides derived from the transcription initiation site, eg, between –10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al (In: Huber B E and B I Carr (1994) *Molecular and Immunologic Approaches*, Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of sequences encoding NABP.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding NABP. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo in vitro and ex vivo therapy. For ex vivo therapy, vectors are introduced into stem cells taken from the patient and clonally propagated for autologous transplant back into that same patient as presented in U.S. Pat. Nos. 5,399,493 and 5,437,994, disclosed herein by reference. Delivery by transfection and by liposome are quite well known in the art.

Furthermore, the nucleotide sequences for NABP disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for NABP can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C M (1993; Blood Rev 7: 127–34) and Trask B J (1991; Trends Genet 7: 149–54).

The technique of fluorescent in situ hybridization of chromosome spreads has been described, among other places, in Verma et al (1988) *Human Chromosomes: A Manual of Basic Techniques*, Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of the gene encoding NABP on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers may be used for extending genetic maps. For example, a sequence tagged site based map of the human genome was recently published by the Whitehead-MIT Center for Genomic Research (Hudson T J et al (1995) Science 270: 1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22-23 (Gatti et al (1988) Nature 336: 577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of NABP, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio of toxic to therapeutic effects is the therapeutic index, which can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

It is contemplated, for example, that NABP or an NABP derivative can be delivered in a suitable formulation to block the progression of Alzheimer's disease and autoimmune disorders, such as SLE. Similarly, administration of NABP antagonists may also inhibit the activity or shorten the lifespan of this protein.

The examples below are provided to illustrate the subject invention and are not included for the purpose of limiting the invention.

EXAMPLES

I cDNA Library Construction

The COLNNOT01 cDNA library was constructed from tissue removed from the normal colon of a 75 year old male. The frozen tissue was immediately homogenized and lysed using a Polytron PT-3000 homogenizer (Brinkmann Instruments Inc, Westbury N.Y.) in guanidinium isothiocyanate buffer. Lysates were then loaded on a 5.7 M CsCl cushion and ultracentrifuged in a SW28 swinging bucket rotor for 18 hours at 25,000 rpm at ambient temperature. The RNA was extracted once with acid phenol and precipitated using 0.3 M sodium acetate and 2.5 volumes of ethanol, resuspended in DEPC-treated water and DNase treated for 25 min at 37° C. The reaction was stopped with an equal volume of acid phenol, and the RNA was isolated using the OLIGOTEX kit (QIAGEN Inc, Chatsworth Calif.) and used to construct the cDNA library.

The RNA was handled according to the recommended protocols in the SUPERSCRIPT plasmid system for cDNA synethsis and plasmid cloning (catalog #18248-013; Gibco/BRL). cDNAs were fractionated on a SEPHAROSE CL4B column (catalog #275105, Pharmacia), and those cDNAs exceeding 400 bp were ligated into PSPORT I. The plasmid PSPORT I was subsequently transformed into DH5E competent cells (Cat. #18258-012, Gibco/BRL).

II Isolation and Sequencing of cDNA Clones

Plasmid DNA was released from the cells and purified using the Miniprep Kit (Catalogue# 77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Catalog# 22711, LIFE TECHNOLOGIES, Gaithersburg Md.) with carbenicillin at 25 mg/L and glycerol at 0.4%; 2) the bacteria were cultured for 24 hours after the wells were inoculated and then lysed with 60 μl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed.

After the last step in the protocol, samples were transferred to a Beckman 96-well block for storage.

The cDNAs were sequenced by the method of Sanger F and AR Coulson (1975; J Mol Biol 94:441f), using a Hamilton MICROLAB 2200 (Hamilton, Reno NV) in combination with four Peltier thermal cyclers (PTC200 from MJ Research, Watertown, Me.) and Applied Biosystems 377 or 373 DNA sequencing systems (Perkin Elmer), and reading frame was determined.

III Homology Searching of cDNA Clones and Their Deduced Proteins

Each cDNA was compared to sequences in GenBank using a search algorithm developed by Applied Biosystems and incorporated into the INHERIT 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 sequence analysis system in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul SF (1993) J Mol Evol 36: 290–300; Altschul, S F et al (1990) J Mol Biol 215: 403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labelled nucleotide sequence to a membrane on which RNAs from a particular cell type or tissue have been bound (Sambrook et al. supra).

Analogous computer techniques using BLAST (Altschul SF 1993 and 1990, supra) are used to search for identical or related molecules in nucleotide databases such as GenBank or the LIFESEQ database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

% sequence identity×% maximum BLAST score/100 and it takes into acccount both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

V Extension of NABP-Encoding Polynucleotides to Full Length or to Recover Regulatory Elements Full length NABP-encoding nucleic acid sequence (SEQ ID NO:2) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known NABP-encoding sequence "outward" generating amplicons containing new, unknown nucleotide sequence for the region of interest (U.S. patent application Ser. No. 08/487,112, filed Jun. 7, 1995, specifically incorporated by reference). The initial primers are designed from the cDNA using OLIGO 4.06 primer analysis software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier thermal cycler (PTC200; MJ Research, Watertown Me.) and the following parameters:

| Step | Condition |
| --- | --- |
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%)

agarose mini-gel to determine which reactions were successful in extending the sequence. Bands thought to contain the largest products were selected and cut out of the gel. Further purification involves using a commercial gel extraction method such as QIAQUICK (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent E. coli cells (in 40 μl of appropriate media) are transformed with 3 μl of ligation mixture and cultured in 80 μl of SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 software (National Biosciences), labeled by combining 50 pmol of each oligomer and 250 mCi of [$\gamma$-$^{32}$P] adenosine triphosphate (Amersham, Chicago Ill.) and T4 polynucleotide kinase (DuPont NEN, Boston Mass.). The labeled oligonucleotides are substantially purified with SEPHADEX G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester N.Y.) is exposed to the blots or the blots are exposed to a PhosphorImager cassette (Molecular Dynamics, Sunnyvale Calif.) for several hours, hybridization patterns are compared visually.

VII Antisense Molecules

The NABP-encoding sequence, or any part thereof, is used to inhibit in vivo or in vitro expression of naturally occurring NABP. Although use of antisense oligonucleotides, comprising about 20 base-pairs, is specifically described, essentially the same procedure is used with larger cDNA fragments. An oligonucleotide based on the coding sequences of NABP, as shown in FIGS. 1A, 1B and 1C is used to inhibit expression of naturally occurring NABP. The complementary oligonucleotide is designed from the most unique 5' sequence as shown in FIGS. 1A, 1B and 1C and used either to inhibit transcription by preventing promoter binding to the upstream nontranslated sequence or translation of an NABP-encoding transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIGS. 1A, 1B and 1C.

VIII Expression of NABP

Expression of the NABP is accomplished by subcloning the cDNAs into appropriate vectors and transfecting the vectors into host cells. In this case, the cloning vector, pSport, previously used for the generation of the cDNA library is used to express NABP in E. coli. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length NABP-encoding sequence. The signal sequence directs the secretion of NABP into the bacterial growth media which can be used directly in the following assay for activity.

IX NABP Activity

NABP binding to RNA or DNA can be assessed by a method described by Zamore et al (1992, supra). $^{32}$P-labelled RNA or DNA and NABP are incubated 1 hour at 25° C. with 20 U RNasin (for RNA only), 1 mg/ml yeast tRNA in 50 mM KCl, 10 mM HEPES-KOH (pH 8.0), 0.025% Nonidet P-40, 1 mM dithiothreitol, and 10% glycerol. DNA-protein or RNA-protein complexes are then analyzed by electrophoresis on polyacrylamide gels.

X Production of NABP Specific Antibodies

NABP substantially purified using PAGE electrophoresis (Sambrook, supra) is used to immunize rabbits and to produce antibodies using standard protocols. The amino acid sequence translated from NABP is analyzed using DNAStar software (DNASTAR Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions (shown in FIG. 4) is described by Ausubel F M et al (supra).

Typically, the oligopeptides are 15 residues in length, synthesized using an Applied Biosystems 431A peptide synthesizer using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring NAP Using Specific Antibodies

Naturally occurring or recombinant NABP is substantially purified by immunoaffinity chromatography using antibodies specific for NABP. An immunoaffinity column is constructed by covalently coupling NABP antibody to an activated chromatographic resin such as CnBr-activated SEPHAROSE (Pharmacia Biotech). After the coupling, the resin is blocked and washed according to the manufacturer's instructions.

Media containing NABP is passed over the immunoaffinity column, and the column is washed under conditions that allow the preferential absorbance of NABP (eg, high ionic strength buffers in the presence of detergent). The column is eluted under conditions that disrupt antibody/NABP binding (eg, a buffer of pH 2–3 or a high concentration of a chaotrope such as urea or thiocyanate ion), and NABP is collected.

XII Identification of Molecules Which Interact with NABP

NABP, or biologically active fragments thereof, are labelled with $^{125}$I Bolton-Hunter reagent (Bolton, A E and Hunter, W M (1973) Biochem J 133: 529). Candidate molecules previously arrayed in the wells of a 96 well plate are incubated with the labelled NABP, washed and any wells with labelled NABP complex are assayed. Data obtained using different concentrations of NABP are used to calculate values for the number, affinity, and association of NABP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A substantially purified polypeptide comprising the amino acid sequence of SEQ ID NO:1.

2. A composition comprising the polypeptide of claim 1 in conjunction with a suitable pharmaceutical carrier.

* * * * *

```
                          SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
              (A) LENGTH: 227 amino acids
              (B) TYPE: amino acid
              (C) STRANDEDNESS: single
              (D) TOPOLOGY: linear (ii) MOLECULE TYPE: peptide (vii) IMMEDIATE SOURCE:
              (A) LIBRARY:
              (B) CLONE: Consensus (xi) SEQUENCE DESCRIPTION: SEQ ID NO:1:

Met Ala Ala Gln Ala Pro Gly Val Ile Thr Gly Val Thr Pro Ala Arg
  1               5                  10                  15

Pro Pro Ile Pro Val Thr Ile Pro Ser Val Gly Val Val Asn Pro Ile
                  20                  25                  30

Leu Ala Ser Pro Pro Thr Leu Gly Leu Leu Glu Pro Lys Lys Glu Lys
              35                  40                  45

Glu Glu Glu Glu Leu Phe Pro Glu Ser Glu Arg Pro Glu Met Leu Ser
      50                  55                  60

Glu Gln Glu His Met Ser Ile Ser Gly Ser Ser Ala Arg His Met Val
  65                  70                  75                  80

Met Gln Lys Leu Leu Arg Lys Gln Glu Ser Thr Val Met Val Leu Arg
                  85                  90                  95

Asn Met Val Asp Pro Lys Asp Ile Asp Asp Asp Leu Glu Gly Glu Val
                  100                 105                 110

Thr Glu Glu Cys Gly Lys Phe Gly Ala Val Asn Arg Val Ile Ile Tyr
              115                 120                 125
```

```
Gln Glu Lys Gln Gly Glu Glu Asp Ala Glu Ile Ile Val Lys Ile
    130                 135                 140

Phe Val Glu Phe Ser Ile Ala Ser Glu Thr His Lys Ala Ile Gln Ala
145                 150                 155                 160

Leu Asn Gly Arg Trp Phe Ala Gly Arg Lys Trp Trp Leu Lys Cys Thr
                165                 170                 175

Thr Arg Ser Val Leu Ile Thr Val Thr Ser Leu Arg Asp Ser Gly Pro
            180                 185                 190

Ser Pro Arg Thr Cys Thr Cys Ser Leu Phe Pro Leu Gly Phe Ile Val
            195                 200                 205

Ile Gln Trp Cys Pro Arg Gly Gln Ala Arg Ser Ala Gln Pro Ser Leu
210                 215                 220

Gln Cys Gly
225

(2) INFORMATION FOR SEQ ID NO:2:

(i) SEQUENCE CHARACTERISTICS:
        (A) LENGTH: 895 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY:
        (B) CLONE: Consensus (xi) SEQUENCE DESCRIPTION: SEQ ID NO:2:

TGCATCACTT ACCACTAGTT TTACATCGTC GTGACTGGTG CAAACCCTAG GCTGTTACCC      60

ACACGTTAAG TCGCCGTTTC AGCACATTAG TTGCCGGAGC AGCGGTGCTG GGTACCCTGG    120

GCACACCTGG ACTGGTGTCC CCAGCACTGA CCCTGGCCCA GCCCCTGGGC ACTTTGCCCC    180

AGGCTGTCAT GGCTGCCCAG GCACCTGGAG TCATCACAGG TGTGACCCCA GCCCGTCCTC    240

CTATCCCGGT CACCATCCCC TCGGTGGGAG TGGTGAACCC CATCCTGGCC AGCCCTCCAA    300

CGCTGGGTCT CCTGGAGCCC AAGAAGGAGA AGGAAGAAGA GGAGCTGTTT CCCGAGTCAG    360

AGCGGCCAGA GATGCTGAGC GAGCAGGAGC ACATGAGCAT CTCGGGCAGT AGCGCCCGAC    420

ACATGGTGAT GCAGAAGCTG CTCCGCAAGC AGGAGTCTAC AGTGATGGTT CTGCGCAACA    480

TGGTGGACCC CAAGGACATC GATGATGACC TGGAAGGGGA GGTGACAGAG GAGTGTGGCA    540

AGTTCGGGGC CGTGAACCGC GTCATCATCT ACCAAGAGAA ACAAGGCGAG GAGGAGGATG    600

CAGAAATCAT TGTCAAGATC TTTGTGGAGT TTTCCATAGC CTCTGAGACT CATAAGGCCA    660

TCCAGGCCCT CAATGGCCGC TGGTTTGCTG GCCGCAAGTG GTGGCTGAAG TGTACGACCA    720

GGAGCGTTTT GATAACAGTG ACCTCTCTGC GTGACAGTGG TCCCTCTCCC CGGACTTGCA    780

CTTGTTCCTT GTTTCCTCTG GGTTTTATAG TGATACAGTG GTGTCCCCGG GGCCAGGCGC    840

GCTCTGCCCA GCCCAGCCTA CAGTGCGGAT AAAGGTGCGG ATGCTGCTGG CCCTG         895

(2) INFORMATION FOR SEQ ID NO:3:

(i) SEQUENCE CHARACTERISTICS:
        (A) LENGTH: 383 amino acids
        (B) TYPE: amino acid
        (C) STRANDEDNESS: single
        (D) TOPOLOGY: linear (ii) MOLECULE TYPE: peptide (vii) IMMEDIATE SOURCE:
```

(A) LIBRARY: GenBank
(B) CLONE: 166694

(xi) SEQUENCE DESCRIPTION: SEQ ID NO:3:

| Met | Leu | Gly | Gly | Leu | Tyr | Gly | Asp | Leu | Pro | Pro | Thr | Asp | Glu |
|---|---|---|---|---|---|---|---|---|---|---|---|---|---|
| 1 | | | | 5 | | | | | 10 | | | | 15 |

Lys Pro Ser Gly Asn Ser Ser Val Trp Ser Arg Ser Thr Lys Met
         20              25              30

Ala Pro Thr Leu Arg Lys Pro Ala Phe Ala Pro Pro Gln Thr
         35              40              45

Ile Leu Arg Pro Leu Asn Lys Pro Lys Pro Ile Val Ser Ala Pro Tyr
50              55              60

Lys Pro Pro Pro Asn Ser Ser Gln Ser Val Leu Ile Pro Ala Asn Glu
65              70              75              80

Ser Ala Pro Ser His Gln Pro Ala Leu Val Gly Val Thr Ser Ser Val
              85              90              95

Ile Glu Glu Tyr Asp Pro Ala Arg Pro Asn Asp Tyr Glu Glu Tyr Lys
              100             105             110

Arg Glu Lys Lys Arg Lys Ala Thr Glu Ala Glu Met Lys Arg Glu Met
              115             120             125

Asp Lys Arg Arg Gln Val Tyr Pro Glu Arg Asp Met Arg Glu Arg Glu
130             135             140

Glu Arg Glu Arg Arg Glu Arg Glu Ile Thr Val Ile Leu Ser Val Asp
145             150             155             160

Ile Ser Gly Glu Glu Arg Gly Arg Asp Pro Ala Arg Val Val Val Glu
              165             170             175

Val Leu Gly Arg Glu Asp Pro Arg Leu Leu Pro Gly Asn Val Asp Gly
              180             185             190

Phe Ser Ile Gly Lys Ser Lys Pro Ser Gly Leu Gly Val Gly Ala Gly
              195             200             205

Gly Gln Met Thr Pro Ala Gln Arg Met Met Pro Lys Met Gly Trp Lys
210             215             220

Gln Gly Gln Gly Leu Gly Lys Ser Glu Gln Gly Ile Pro Thr Pro Leu
225             230             235             240

Met Ala Lys Lys Thr Asp Arg Arg Ala Gly Val Ile Val Asn Ala Ser
              245             250             255

Glu Asn Lys Ser Ser Ser Ala Glu Lys Lys Val Val Lys Ser Val Asn
              260             265             270

Ile Asn Gly Glu Pro Thr Arg Val Leu Leu Leu Arg Asn Met Val Gly
              275             280             285

Pro Gly Gln Val Asp Asp Glu Leu Glu Asp Glu Val Gly Gly Glu Cys
290             295             300

Ala Lys Tyr Gly Thr Val Thr Arg Val Leu Ile Phe Glu Ile Thr Glu
305             310             315             320

Pro Asn Phe Pro Val His Glu Ala Val Arg Ile Phe Val Gln Phe Ser
              325             330             335

Arg Pro Glu Glu Thr Thr Lys Ala Leu Val Asp Leu Asp Gly Arg Tyr
              340             345             350

Phe Gly Gly Arg Thr Val Arg Ala Thr Phe Tyr Asp Glu Glu Lys Phe
              355             360             365

Ser Lys Asn Glu Leu Ala Pro Val Pro Gly Glu Ile Pro Gly Tyr
              370             375             380

(2) INFORMATION FOR SEQ ID NO:4:

(i) SEQUENCE CHARACTERISTICS:
        (A) LENGTH: 475 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 267188

(xi) SEQUENCE DESCRIPTION: SEQ ID NO:4:

```
Met Ser Asp Phe Asp Glu Phe Glu Arg Gln Leu Asn Glu Asn Lys Gln
 1               5                  10                  15

Glu Arg Asp Lys Glu Asn Arg His Arg Lys Arg Ser His Ser Arg Ser
            20                  25                  30

Arg Ser Arg Asp Arg Lys Arg Ser Arg Ser Arg Asp Arg Arg Asn
        35                  40                  45

Arg Asp Gln Arg Ser Ala Ser Arg Asp Arg Arg Arg Ser Lys Pro
50                  55                  60

Leu Thr Arg Gly Ala Lys Glu Glu His Gly Gly Leu Ile Arg Ser Pro
65                  70                  75                  80

Arg His Glu Lys Lys Lys Val Arg Lys Tyr Trp Asp Val Pro Pro
                85                  90                  95

Pro Gly Phe Glu His Ile Thr Pro Met Gln Tyr Lys Ala Met Gln Ala
            100                 105                 110

Ala Gly Gln Ile Pro Ala Thr Ala Leu Leu Pro Thr Met Thr Pro Asp
            115                 120                 125

Gly Leu Ala Val Thr Pro Thr Pro Val Pro Val Val Gly Ser Gln Met
130                 135                 140

Thr Arg Gln Ala Arg Arg Leu Tyr Val Gly Asn Ile Pro Phe Gly Ile
145                 150                 155                 160

Thr Glu Glu Ala Met Met Asp Phe Phe Asn Ala Gln Met Arg Leu Gly
                165                 170                 175

Gly Leu Thr Gln Ala Pro Gly Asn Pro Val Leu Ala Val Gln Ile Asn
            180                 185                 190

Gln Asp Lys Asn Phe Ala Phe Leu Glu Phe Arg Ser Val Asp Glu Thr
        195                 200                 205

Thr Gln Ala Met Ala Phe Asp Gly Ile Ile Phe Gln Gly Gln Ser Leu
210                 215                 220

Lys Ile Arg Arg Pro His Asp Tyr Gln Pro Leu Pro Gly Met Ser Glu
225                 230                 235                 240

Asn Pro Ser Val Tyr Val Pro Gly Val Val Ser Thr Val Val Pro Asp
                245                 250                 255

Ser Ala His Lys Leu Phe Ile Gly Gly Leu Pro Asn Tyr Leu Asn Asp
            260                 265                 270

Asp Gln Val Lys Glu Leu Leu Thr Ser Phe Gly Pro Leu Lys Ala Phe
        275                 280                 285

Asn Leu Val Lys Asp Ser Ala Thr Gly Leu Ser Lys Gly Tyr Ala Phe
290                 295                 300

Cys Glu Tyr Val Asp Ile Asn Val Thr Asp Gln Ala Ile Ala Gly Leu
305                 310                 315                 320

Asn Gly Met Gln Leu Gly Asp Lys Lys Leu Leu Val Gln Arg Ala Ser
                325                 330                 335
```

-continued

```
Val Gly Ala Lys Asn Ala Thr Leu Val Ser Pro Pro Ser Thr Ile Asn
        340                 345                 350

Gln Thr Pro Val Thr Leu Gln Val Pro Gly Leu Met Ser Ser Gln Val
        355                 360                 365

Gln Met Gly Gly His Pro Thr Glu Val Leu Cys Leu Met Asn Met Val
370                 375                 380

Leu Pro Glu Glu Leu Leu Asp Asp Glu Glu Tyr Glu Glu Ile Val Glu
385                 390                 395                 400

Asp Val Arg Asp Glu Cys Ser Lys Tyr Gly Leu Val Lys Ser Ile Glu
                405                 410                 415

Ile Pro Arg Pro Val Asp Gly Val Glu Val Pro Gly Cys Gly Lys Ile
                420                 425                 430

Phe Val Glu Phe Thr Ser Val Phe Asp Cys Gln Lys Ala Met Gln Gly
                435                 440                 445

Leu Thr Gly Arg Lys Phe Ala Asn Arg Val Val Thr Lys Tyr Cys
450                 455                 460

Asp Pro Asp Ser Tyr His Arg Arg Asp Phe Trp
465                 470                 475

(2) INFORMATION FOR SEQ ID NO:5:

(i) SEQUENCE CHARACTERISTICS:
        (A) LENGTH: 416 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 627165

(xi) SEQUENCE DESCRIPTION: SEQ ID NO:5:

Met Gly Tyr Asp Asp Arg Glu Arg Asp Arg Glu Arg Arg His Arg
1                   5                  10                  15

Ser Arg Ser Arg Asp Arg His Arg Glu Arg Ser Arg Asp Arg His
            20                  25                  30

His Arg Asn Ser Arg Arg Lys Pro Ser Leu Tyr Trp Asp Val Pro Pro
            35                  40                  45

Pro Gly Phe Glu His Ile Thr Pro Met Gln Tyr Lys Ala Met Gln Ala
50                  55                  60

Ser Gly Gln Ile Pro Ala Ser Val Val Pro Asp Thr Pro Gln Thr Ala
65                  70                  75                  80

Val Pro Val Val Gly Ser Thr Ile Thr Arg Gln Ala Arg Arg Leu Tyr
                85                  90                  95

Val Gly Asn Ile Pro Phe Gly Val Thr Glu Glu Glu Met Met Glu Phe
                100                 105                 110

Phe Asn Gln Gln Met His Leu Val Gly Leu Ala Gln Ala Ala Gly Ser
            115                 120                 125

Pro Val Leu Ala Cys Gln Ile Asn Leu Asp Lys Asn Phe Ala Phe Leu
            130                 135                 140

Glu Phe Arg Ser Ile Asp Glu Thr Thr Gln Ala Met Ala Phe Asp Gly
145                 150                 155                 160

Ile Asn Leu Lys Gly Gln Ser Leu Lys Ile Arg Arg Pro His Asp Tyr
                165                 170                 175

Gln Pro Met Pro Gly Ile Thr Asp Thr Pro Ala Ile Lys Pro Ala Val
                180                 185                 190
```

-continued

```
Val Ser Ser Gly Val Ile Ser Thr Val Val Pro Asp Ser Pro His Lys
        195                 200                 205
Ile Phe Ile Gly Gly Leu Pro Asn Tyr Leu Asn Asp Asp Gln Val Lys
    210                 215                 220
Glu Leu Leu Leu Ser Phe Gly Lys Leu Arg Ala Phe Asn Leu Val Lys
225                 230                 235                 240
Asp Ala Ala Thr Gly Leu Ser Lys Gly Tyr Ala Phe Cys Glu Tyr Val
                245                 250                 255
Asp Leu Ser Ile Thr Asp Gln Ser Ile Ala Gly Leu Asn Gly Met Gln
                260                 265                 270
Leu Gly Asp Lys Lys Leu Ile Val Gln Arg Ala Ser Val Gly Ala Lys
        275                 280                 285
Asn Ala Gln Asn Ala Ala Asn Thr Thr Gln Ser Val Met Leu Gln Val
        290                 295                 300
Pro Gly Leu Ser Asn Val Val Thr Ser Gly Pro Pro Thr Glu Val Leu
305                 310                 315                 320
Cys Leu Leu Asn Met Val Thr Pro Asp Glu Leu Arg Asp Glu Glu Glu
                325                 330                 335
Tyr Glu Asp Ile Leu Glu Asp Ile Lys Glu Glu Cys Thr Lys Tyr Gly
                340                 345                 350
Val Val Arg Ser Val Glu Ile Pro Arg Pro Ile Glu Gly Val Glu Val
        355                 360                 365
Pro Gly Cys Gly Lys Val Phe Val Glu Phe Asn Ser Val Leu Asp Cys
370                 375                 380
Gln Lys Ala Gln Gln Ala Leu Thr Gly Arg Lys Phe Ser Asp Arg Val
385                 390                 395                 400
Val Val Thr Ser Tyr Phe Asp Pro Asp Lys Tyr His Arg Arg Glu Phe
                405                 410                 415
```